US006864356B2

(12) United States Patent
Sloane

(10) Patent No.: US 6,864,356 B2
(45) Date of Patent: Mar. 8, 2005

(54) SIXTEEN AMINO ACID OF THE ANTINEOPLASTIC PROTEIN (ANUP) AS A PHARMACOLOGICALLY ACTIVE ANTI-TUMOR AGENT

(76) Inventor: Nathan Howard Sloane, 1842 Brookside Dr., Germantown, TN (US) 38138

( * ) Notice: Subject to any disclaimer, the term of this patent is extended or adjusted under 35 U.S.C. 154(b) by 0 days.

(21) Appl. No.: 08/986,606

(22) Filed: Dec. 8, 1997

(65) Prior Publication Data

US 2002/0061851 A1 May 23, 2002

(51) Int. Cl.[7] .................................................. C07K 7/00
(52) U.S. Cl. ........................................ 530/326; 514/13
(58) Field of Search ........................... 530/326; 514/13, 514/2

(56) References Cited

U.S. PATENT DOCUMENTS 5,298,604 A  *  3/1994  Sloane ....................... 530/351

OTHER PUBLICATIONS

Ridge et al, *Cytokine*, vol. 8 No. 1, Jan. 1996, pp 1–5.*

* cited by examiner

*Primary Examiner*—Jon Weber
*Assistant Examiner*—David Lukton
(74) *Attorney, Agent, or Firm*—Mintz, Levin, Cohn, Ferris, Glovsky and Popeo, P.C.; Ingrid A. Beattie

(57) ABSTRACT

The invention provides a 16 amino acid peptide representing the partial N-terminal amino acid sequence of the Antineoplastic Protein (ANUP). The 16 amino acid peptide provided is a highly active pharmacologically antitumor agent.

8 Claims, No Drawings

SIXTEEN AMINO ACID OF THE ANTINEOPLASTIC PROTEIN (ANUP) AS A PHARMACOLOGICALLY ACTIVE ANTI-TUMOR AGENT

FIELD OF THE INVENTION

The present invention relates to the use of the 16 amino acid peptide which represents the partial N-terminal amino acid sequence of the Antineoplastic Protein (ANUP) as a pharmacologically active antitumor agent.

BACKGROUND OF THE INVENTION

The Antineoplastic Protein (ANUP) kills tumor cells. The protein (ANUP) in the purified state has been implicated in regression of both HeLa (human cervical tumor all line) and KB (human laryngeal cell line) implanted in nude mice.

SUMMARY OF THE INVENTION

The present invention describes the pharmacologically active anti-tumor activity of the 16 amino acid peptide which represents the partial N-terminal amino acid sequence of the Antineoplastic Protein (ANUP).

The 16 amino acid peptide is approximately one-half as active as the protein on a molar basis utilizing the human breast tumor cell line (MDA 231). However, only about one-tenth of the weight of the peptide is required when compared to the amount of protein for equivalent activity against the human breast tumor cell line. Both the protein and the peptide exert their action by killing tumor cells (apoptosis) since electron microscopy studies showed complete degradation of the cells (Struve et al. Cancer Res. Therapy and Control (1990) 1: pp 224–230).

DETAILED DESCRIPTION OF THE INVENTION

The present invention relates to the use of the 16 amino acid peptide which represents the partial N-terminal amino acid sequence of the Antineoplastic Protein (ANUP) as a pharmacologically active antitumor agent. The peptide is about 50% as active as the protein per se but only about one-tenth of the weight of the peptide is equivalent in activity of the protein (ANUP) on a molar basis (ca $10^{-9}$ M).

DESCRIPTION OF THE PREFERRED EMBODIMENT

The 16 Amino Acid Peptide

The synthetic hexadeca peptide (16 L-amino acids) has the following sequence:

| 1. | Pyroglu | |
| 2. | Leu | L |
| 3. | Lys | K |
| 4. | Cys | C |
| 5. | Tyr | Y |
| 6. | Thr | T |
| 7. | Cys | C |
| 8. | Lys | K |
| 9. | Glu | E |
| 10. | Pro | P |
| 11. | Met | M |
| 12. | Thr | T |
| 13. | Ser | S |
| 14. | Ala | A |
| 15. | Ala | A |
| 16. | Cys | C (SEQ ID NO: 1) |

The peptide was synthesized by Research Genetics Inc., in Huntsville, Ala. 35801; the peptide was pure as shown by HPLC (high performance liquid chromatography) and the molecular weight was check by mass spectrometry (MS).

The 16 amino acid peptide representing the partial N-terminal amino acid sequence of the Antineoplastic Protein (ANUP) is a highly active pharmacologically antitumor agent. The 16 amino acid peptide is about 50% as active as antitumor agent compared to the antitumor active as the protein (ANUP) per se when tested as a tumor killer agent (in vitro) utilizing human breast tumor cell line (MDA 231). The protein (ANUP) in the purified state also shows regression of both HeLa (human cervical tumor all line) and KB (human laryngeal cell line) implanted in nude mice (Sloane, Davis Tumor Targeting (1996) 2, pp 322–326). The nonapeptide is about 10% as active compared to the antineoplastic protein (ANUP) in the human breast tumor cell line in vitro assay system. Both peptides, the 9 amino acid peptide and the 16 amino acid peptide require presence of the detergent sodium dodecyl sulfate to activate the peptides for full pharmacological antitumor activity.

EXAMPLES

Example 1

The Pharmacological Anti-tumor Activity of the 16 Amino Acid Peptide ($P_{16}$)

The antitumor activity of the peptide ($P_{16}$) was assayed against the human breast tumor cell line (MDA 231) and its activity was compared to the in vitro antitumor effect of the "pure" protein (ANUP).

The assay for the pharmacological antitumor activities were performed as follows utilizing 96 well plates—

20,300–30,000 human breast tumor cells in L-15 medium (200 µl) containing 2.5% fetal calf serum and 100 µg gentamycin per ml (complete medium) were incubated at 37° in air for 120 hours; after this incubation period 50 µl of serially diluted $P_{16}$ and ANUP were added to each well. The serial dilutions were prepared as follows: 2 mg each (the $P_{16}$ ANUP) were dissolved in 2 ml of complete medium containing 0.05% sodium dodecyl sulfate (SDS). The solutions were diluted in complete medium containing 0.05% SDS to a concentration of 350 µg per ml.

Dilution plates were prepared as follows:

100 µl of complete medium were added to each well and 50 µl of diluted $P_{16}$ and ANUP were added to each well in row A thus 1.3 dilution was accomplished; 50 µl were serially diluted in the 100 μl of medium in rows B through H. Thus the range of concentrations were from 6 μg to 2 mg when 50 μl each dilution series were added to the 200 μl of the complete medium containing the MDA cells. The plates were incubated for an additional 96–120 hours. The medium was poured off and after a 90-minute incubation with 50 μl neutral red dye (0.5 ml neutral red (0.25% ethanol (0.6 ml) diluted 5.5 saline-0.16 mm HCl) the cells were washed twice with PBS (phosphate buffer saline) at room temperature. The concentration of living cells (since only living cells absorb the dye) was determined after adding 100 μl lysing buffer (50% ethanol in 0.05 m $NaH_2 PO_4$) the concentration of

|  | Fraction of the Activity relative to ANUP |
|---|---|
| $P_{16}$ no SDS | ± no Activity |
| $P_{16}$ + 0.005% SDS | 0.04 |
| $P_{16}$ + 0.02% SDS | 0.50 |
| $P_{16}$ + 0.05% SDS | 0.50 | neutral red released in each well was determined using a Dynetech plate reader set at 550 mm. A unit of activity was defined as the concentration of ANUP and $P_{16}$ for 50% killing.

Under these assay conditions the 50% end points were as follows:

ANUP 0.1 μg/well=1.25×10$^{-8}$ M $P_{16}$ 0.0 μg/well=2.2×10$^{-8}$ M

Thus, $P_{16}$ is about 50% as active as ANUP on a molar basis; whereas on a weight basis only one tenth of the peptide weight is equal in activity 10 times the weight of the protein (ANUP).

In the absence of SDS neither the peptide nor the protein showed any antitumor activity. Thus the detergent is probably necessary to form the correct geometrical shape for activity as described by Sloane and Davis Tumor Targeting (1996) 2, 322–326. The data utilizing $P_{16}$ as an antitumor agent against the human breast tumor cell line (MDA 231) are as follows:

What is claimed is:

1. A purified synthetic polypeptide consisting of the amino acid sequence: PyroGlu-LKCYTCKEPMTSAAC (SEQ ID NO: 1).

2. An anti-tumor polypeptide consisting of the amino acid sequence: PyroGlu-LKCYTCKEPMTSAAC (SEQ ID NO: 1), wherein said polypeptide induces apoptosis of a breast tumor cell.

3. The polypeptide of claim 2, wherein said anti-tumor polypeptide is activated by contacting said polypeptide with sodium dodecyl sulfate (SDS).

4. A method of killing a tumor cell, comprising contacting said breast tumor cell with a polypeptide consisting of the amino acid sequence: PyroGlu-LKCYTCKEPMTSAAC (SEQ ID NO: 1) for a time and under conditions effective to promote killing by apoptosis of said tumor cell.

5. The method of claim 4, wherein said tumor is a breast tumor.

6. A method of activating an anti-tumor polypeptide, comprising contacting said polypeptide with sodium dodecyl sulfate, wherein an anti-tumor activity of said polypeptide is activated after said contacting step, wherein said polypeptide consists of the amino acid sequence: PyroGlu-LKCYTCKEPMTSAAC (SEQ ID NO: 1), and wherein the activated anti-tumor polypeptide promotes apoptosis of a breast tumor cell.

7. An SDS-activated anti-tumor polypeptide consisting of the amino acid sequence: PyroGlu-LKCYTCKEPMTSAAC (SEQ ID NO: 1).

8. A method of killing a tumor cell, comprising contacting said breast tumor cell with an SDS-activated polypeptide for a time and under conditions effective to promote killing by apoptosis of said tumor cell, said polypeptide consisting of the amino acid: PyroGlu-LKCYTCKEPMTSAAC (SEQ ID NO: 1).

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Artificial
<220> FEATURE:
<223> OTHER INFORMATION: the partial N-terminal amino acid sequence of
      the Antineoplastic Protein (ANUP)
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 1

Glu Leu Lys Cys Tyr Thr Cys Lys Glu Pro Met Thr Ser Ala Ala Cys
1               5                   10                  15